USOO5597416A

United States Patent [19]
Fuisz et al.

[11] Patent Number: 5,597,416
[45] Date of Patent: *Jan. 28, 1997

[54] METHOD OF MAKING CRYSTALLINE SUGAR AND PRODUCTS RESULTING THEREFROM

[75] Inventors: Richard C. Fuisz, Great Falls; Gerald E. Battist; Garry L. Myers, both of Reston, all of Va.

[73] Assignee: Fuisz Technologies Ltd., Chantilly, Va.

[*] Notice: The portion of the term of this patent subsequent to Sep. 10, 2013, has been disclaimed.

[21] Appl. No.: 133,669

[22] Filed: Oct. 7, 1993

[51] Int. Cl.$^6$ ................................ C13F 3/00; C13F 9/02
[52] U.S. Cl. ............................ 127/30; 127/58; 127/59
[58] Field of Search .............................. 127/30, 58, 59

[56] References Cited

U.S. PATENT DOCUMENTS

| | | | |
|---|---|---|---|
| 2,826,169 | 3/1958 | Le Veen | 119/1 |
| 2,918,404 | 12/1959 | Mende et al. | 167/58 |
| 3,019,745 | 2/1962 | Du Bois et al. | 107/8 |
| 3,036,532 | 5/1962 | Bowe | 107/8 |
| 3,067,743 | 12/1962 | Merton et al. | 128/70 |
| 3,070,045 | 12/1962 | Bowe | 107/8 |
| 3,073,262 | 1/1963 | Bowe | 107/8 |
| 3,095,258 | 6/1963 | Scott | 18/54 |
| 3,118,396 | 1/1964 | Brown et al. | 107/8 |
| 3,131,428 | 5/1964 | Mika | 18/8 |
| 3,308,221 | 3/1967 | Opfell | 264/174 |
| 3,324,061 | 6/1967 | Tanquary et al. | 260/29.2 |
| 3,482,998 | 12/1969 | Carroll et al. | 99/108 |
| 3,523,889 | 8/1970 | Eis | 210/20 |
| 3,557,717 | 1/1971 | Chivers | 107/54 |
| 3,595,675 | 7/1971 | Ash et al. | 99/130 |

(List continued on next page.)

FOREIGN PATENT DOCUMENTS

| | | | |
|---|---|---|---|
| 609137 | 4/1988 | Australia | A61K 9/00 |
| 609135 | 4/1988 | Australia | A61K 7/48 |
| 900605 | 11/1977 | Belgium . | |
| 1303511 | 4/1988 | Canada | A61K 7/42 |
| 0287488A1 | 3/1988 | European Pat. Off. | A61K 9/20 |
| 0387950A1 | 8/1990 | European Pat. Off. | B01D 1/18 |
| 88/2771 | 4/1988 | South Africa . | |
| 90/2139 | 3/1990 | South Africa . | |
| 489211 | 7/1968 | Switzerland | A23G 1/00 |
| 519858 | 5/1971 | Switzerland | A23G 1/00 |
| 2155934 | 3/1985 | United Kingdom | C13K 1/10 |
| WO91/18613 | 5/1991 | WIPO | A61K 31/74 |

OTHER PUBLICATIONS

R. H. Doremus, "Crystallization of Sucrose from Aqueous Solution," *Journal of Colloid and Interface Science*, 104, pp. 114–120 (1985).

P. Bennema, "Surface Diffusion and the Growth of Sucrose Crystals," *Journal of Crystal Growth*, 3,4 pp. 331–334 (1968).

T. D. Simpson, et al., "Crystalline Forms of Lactose Produced in Acidic Alcoholic Media," *Journal of Food Science*, 47, pp. 1948–1954 (1982).

A. D. Randolph, et al., "Continuous Sucrose Nucleation", *The International Sugar Journal*, pp. 8–12 (1974).

(List continued on next page.)

*Primary Examiner*—E. Rollins Cross
*Assistant Examiner*—Patricia L. Hailey
*Attorney, Agent, or Firm*—Hoffmann & Baron

[57] ABSTRACT

The present invention is a new crystalline sugar product and method of making same which includes forming a bi-dimensionally stabilized sugar crystalline frame from an outer portion of an amorphous shearform sugar mass, and, subsequently, converting the remaining portion of the mass to a substantially completely crystalline structure which retains the cross-sectional dimension of the sugar crystalline frame. The present invention also includes co-crystallizing an additive, especially a bio-affecting additive, during the process to provide a co-crystallized product. The structure of the crystallized product can also be loaded with a non-solvent liquid by force of capillary action in the space created within the structure during the conversion from amorphous mass to crystalline structure.

28 Claims, 8 Drawing Sheets

U.S. PATENT DOCUMENTS

| | | |
|---|---|---|
| 3,615,671 | 10/1971 | Schoaf .................................. 99/78 |
| 3,625,214 | 12/1971 | Higuchi ................................ 128/260 |
| 3,676,148 | 7/1972 | De Weese et al. .................... 99/1 |
| 3,723,134 | 3/1973 | Chivers ................................. 99/134 |
| 3,762,846 | 10/1973 | Chivers ................................. 425/7 |
| 3,766,165 | 10/1973 | Rennhard ............................. 260/209 R |
| 3,856,443 | 12/1974 | Salvi ..................................... 425/9 |
| 3,875,300 | 4/1975 | Homm et al. ......................... 424/78 |
| 3,876,794 | 4/1975 | Rennhard ............................. 426/152 |
| 3,925,525 | 12/1975 | LaNieve ............................... 264/40 |
| 3,930,043 | 12/1975 | Warning et al. ...................... 426/515 |
| 3,951,821 | 4/1976 | Davidson ............................. 252/1 |
| 3,967,623 | 7/1976 | Butterworth et al. ................ 128/287 |
| 3,972,725 | 8/1976 | Nicol .................................... 127/58 |
| 3,981,739 | 9/1976 | Dmitrovsky et al. ................ 127/60 |
| 3,992,265 | 11/1976 | Hansen ................................. 195/127 |
| 4,056,364 | 11/1977 | Dmitrovsky et al. ................ 23/273 R |
| 4,086,418 | 4/1978 | Turbak et al. ........................ 536/30 |
| 4,090,920 | 5/1978 | Studer, Jr. ............................. 195/127 |
| 4,136,145 | 1/1979 | Fuchs et al. .......................... 264/164 |
| 4,153,512 | 5/1979 | Messner et al. ...................... 195/103.5 K |
| 4,159,210 | 6/1979 | Chen et al. ........................... 127/29 |
| 4,199,373 | 4/1980 | Dwivedi et al. ...................... 127/30 |
| 4,293,570 | 10/1981 | Vadasz ................................. 426/3 |
| 4,303,684 | 12/1981 | Pitchon et al. ....................... 426/312 |
| 4,338,350 | 7/1982 | Chen et al. ........................... 426/658 |
| 4,348,420 | 9/1982 | Lynch et al. ......................... 426/272 |
| 4,362,757 | 12/1982 | Chen et al. ........................... 426/599 |
| 4,371,516 | 2/1983 | Gregory et al. ...................... 424/22 |
| 4,376,743 | 3/1983 | Dees ..................................... 264/103 |
| 4,382,967 | 5/1983 | Koshida et al. ...................... 426/96 |
| 4,492,685 | 1/1985 | Keith et al. ........................... 424/28 |
| 4,496,592 | 1/1985 | Kuwahara et al. ................... 426/5 |
| 4,500,546 | 2/1985 | Turbak et al. ........................ 514/781 |
| 4,511,584 | 4/1985 | Percel et al. .......................... 426/99 |
| 4,526,525 | 7/1985 | Oiso et al. ............................ 425/9 |
| 4,585,797 | 4/1986 | Cioca .................................... 514/773 |
| 4,619,833 | 10/1986 | Anderson ............................. 426/548 |
| 4,772,477 | 9/1988 | Weiss et al. .......................... 426/99 |
| 4,793,782 | 12/1988 | Sullivan ............................... 425/7 |
| 4,855,326 | 8/1989 | Fuisz .................................... 514/777 |
| 4,872,821 | 10/1989 | Weiss ................................... 425/9 |
| 4,873,085 | 10/1989 | Fuisz .................................... 424/400 |
| 4,879,108 | 11/1989 | Yang et al. ........................... 424/440 |
| 4,885,281 | 12/1989 | Hanstein et al. ..................... 514/53 |
| 4,978,537 | 12/1990 | Song ..................................... 426/5 |
| 4,997,856 | 3/1991 | Fuisz .................................... 514/777 |
| 5,011,532 | 4/1991 | Fuisz .................................... 106/215 |
| 5,028,632 | 7/1991 | Fuisz .................................... 514/772 |
| 5,034,421 | 7/1991 | Fuisz .................................... 514/772 |
| 5,073,387 | 12/1991 | Whistler .............................. 426/7 |
| 5,082,682 | 1/1992 | Peterson .............................. 426/564 |
| 5,082,684 | 1/1992 | Fung .................................... 426/602 |
| 5,084,295 | 1/1992 | Whelan et al. ....................... 426/565 |
| 5,089,606 | 2/1992 | Cole et al. ............................ 536/54 |
| 5,094,872 | 3/1992 | Furcsik et al. ....................... 426/578 |
| 5,096,492 | 3/1992 | Fuisz .................................... 106/215 |
| 5,104,674 | 4/1992 | Chen et al. ........................... 426/573 |
| 5,110,614 | 5/1992 | Corbin et al. ........................ 426/555 |
| 5,236,734 | 8/1993 | Fuisz .................................... 426/641 |
| 5,266,335 | 11/1993 | Cherukuri et al. ................... 426/3 |

OTHER PUBLICATIONS

K. B. Domovs, et al., "Methanol–Soluble Complexes of Lactose and of other Carbohydrates," *J. Dairy Science*, 43, pp. 1216–1223 (1960).

A. D. Randolph, et al., "Continuous Sucrose Nucleation", *The International Sugar Journal*, pp. 35–38 (1974).

A. D. Randoph, et al., "Continuous Sucrose Nucleation", *The International Sugar Journal*, pp. 73–77 (1974).

ICI Americas Inc., "ICI Americas Products for Cosmetics and Pharmaceuticals", (1977).

Domino Sugar Corporation, "Co–crystallization,". (1992?).

Domino Sugar Corporation, "Raspberry", (1992).

Domino Sugar Corporation, "Molasses Dark". (1992).

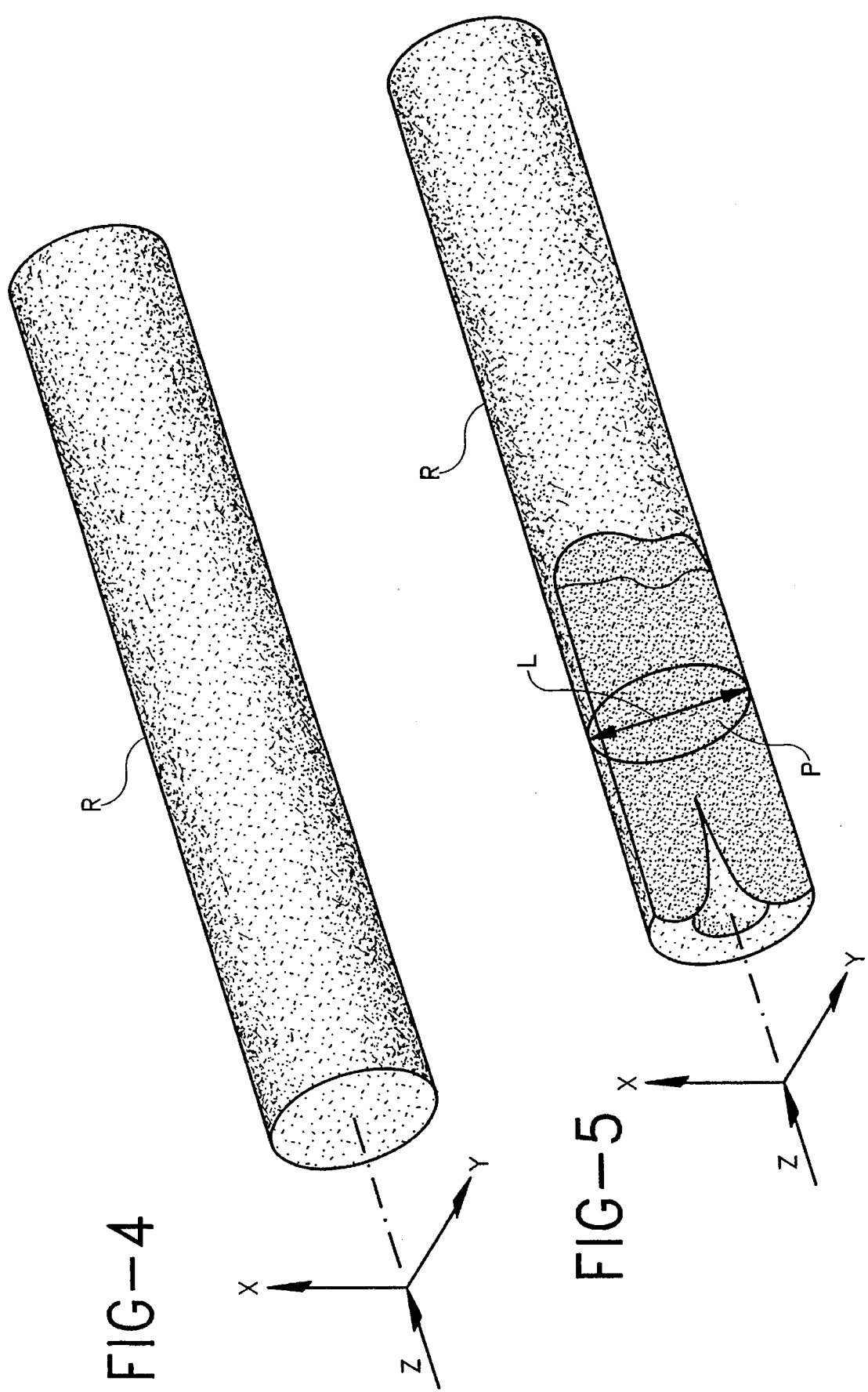

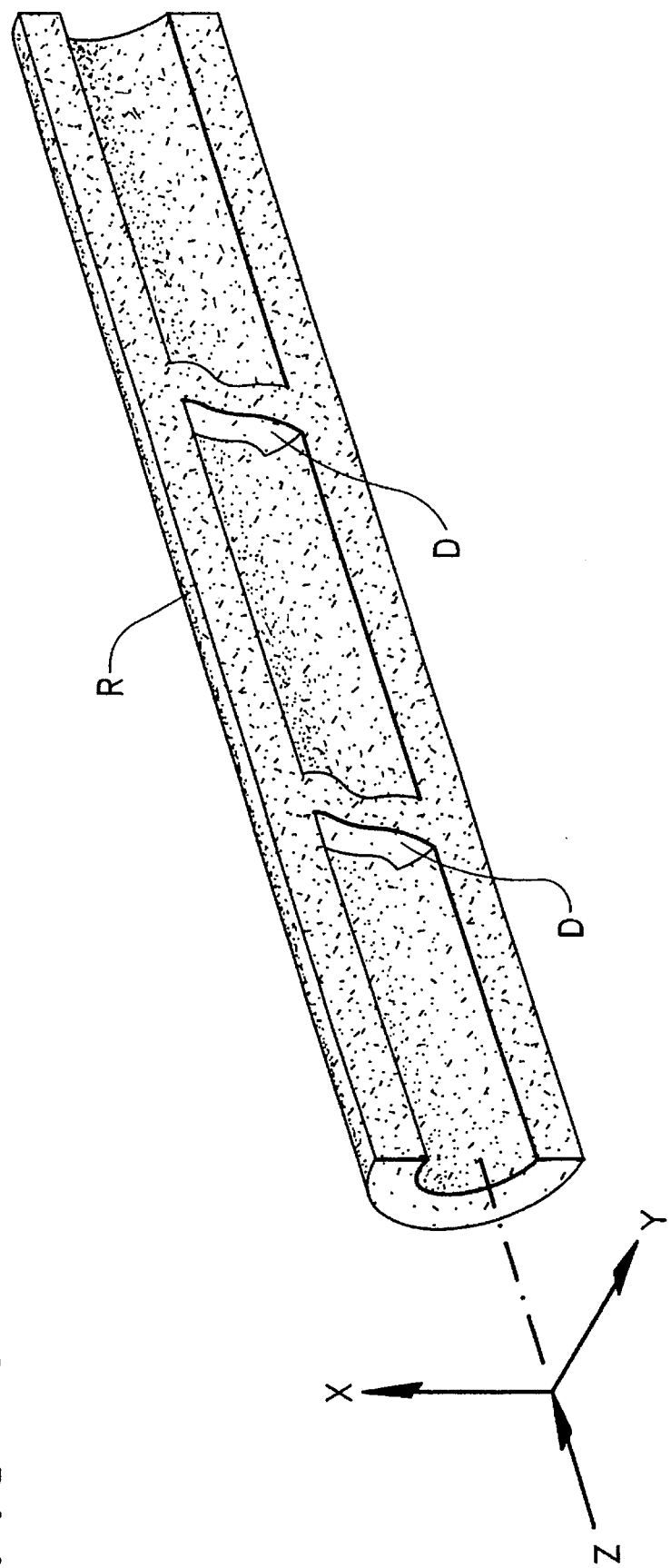

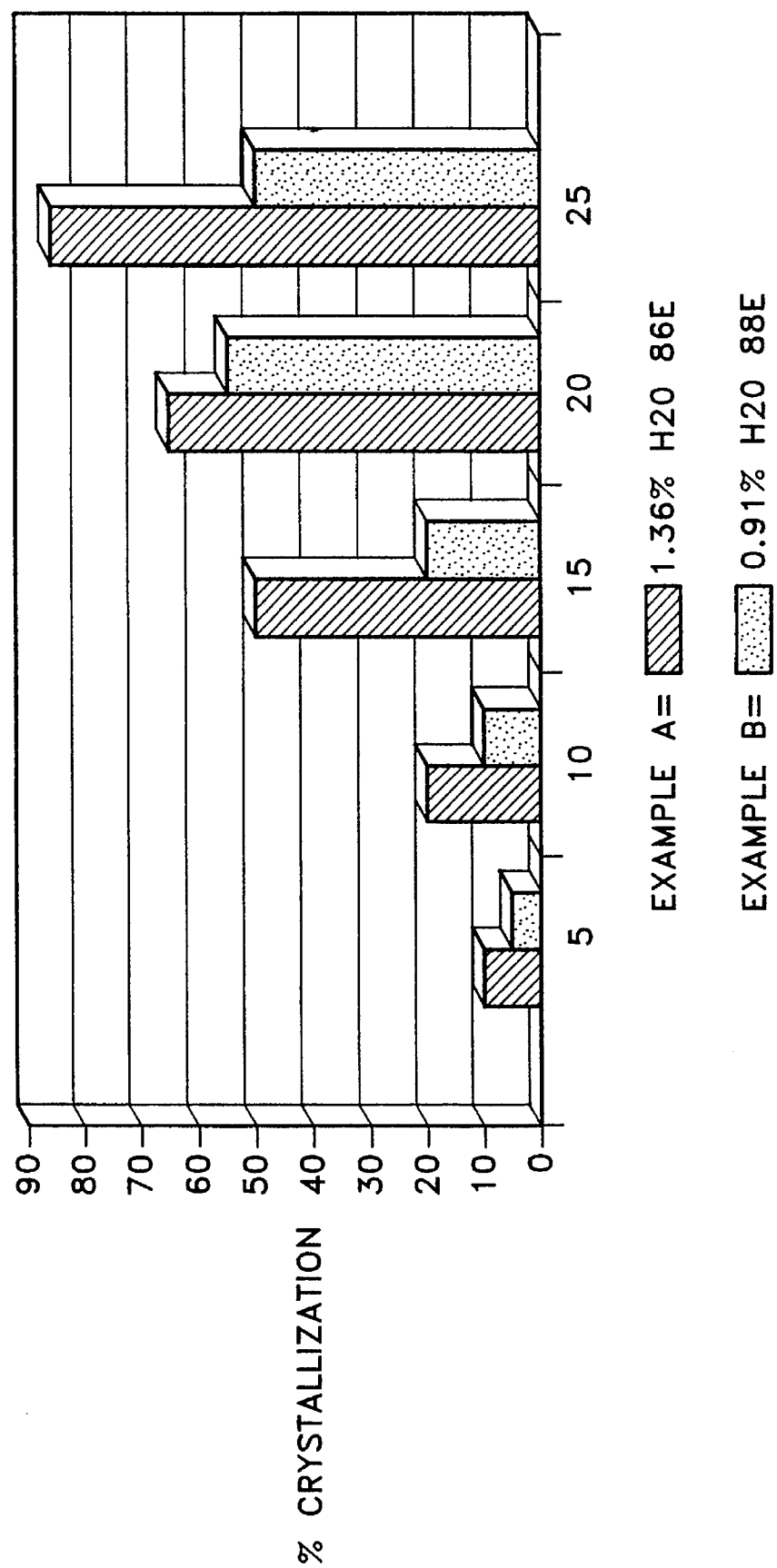

METHOD OF MAKING CRYSTALLINE SUGAR AND PRODUCTS RESULTING THEREFROM

BACKGROUND OF THE INVENTION

The present invention relates to a method of preparing crystalline sugar which provides unique structure and controlled crystal size, and the product resulting therefrom.

Crystallization is one of the oldest industrial chemical transformation processes known. Vast quantities of crystalline substances are produced for commercial purposes, e.g., in excess of $100 \times 10^6$ metric tons per year. One of the most common products prepared by crystallization is sugar.

Crystallization of sugar is complex. The growth of crystals involves simultaneous transfer of heat and mass in a multi-phase, multi-component system. While the coexistence of these conditions alone present complex control problems, fluid and particle mechanics and thermodynamic instability create further complications.

Conventional wisdom in the science of sugars teaches crystallization by supersaturation. Supersaturation requires removal of water. Cooling, evaporating, and precipitating are used. Manufacturing procedures for crystallizing sugar are heat and energy intensive. Moreover, nucleation of sugar crystals during supersaturation is relatively uncontrollable. Consequently, the size and shape of the resulting crystals are unpredictable.

The drawbacks of known sugar manufacturing procedures are especially manifested when preparing sugar having reduced-size crystals. Reduced-size crystalline sugar product is referred to herein as microcrystals. Individual particles of microcrystalline product are no greater than 50 μm.

For example, one method of manufacturing reduced-size crystals involves grinding and sieving crystalline sugar. Grinding is energy intensive. Moreover, fracturing sugar results in a wide distribution of ground sugar crystals. The large crystals must be reground and sieved. Much of the product is lost as fines. Thus, grinding and sieving is expensive and inefficient.

U.S. Pat. No. 3,981,739 to Dmitrovsky, et al. discloses preparation of crystalline sugar from solution by 1) concentrating a solute in the presence of seed crystals added thereto, followed by 2) further removal of solvent through heating and evaporation of the stream resulting from the first stage concentration. This energy intensive procedure produces sugar crystals having an average size in the range of 325–425 microns. The Dmitrovsky, et al. '739 disclosure is a solution process which relies on nucleation by addition of seed crystals while concentrating by high heat and vacuum evaporation. The same procedure is disclosed in U.S. Pat. No. 4,056,364 to Dmitrovsky, et al.

U.S. Pat. No. 4,159,210 to Chen, et al. describes a method for preparing crystallized maple sugar product by 1) concentrating maple syrup to a solids content of about 93–98% in the presence of heat and partial vacuum, and 2) impact heating until transformation and crystallization of the syrup occur. The product may then be cooled, milled and screened to a suitable size range. The Chen, et al. '210 procedure is energy intensive, relies on "beating" to induce nucleation of the crystals, and calls for subsequent milling to obtain reduced-size crystals.

In U.S. Pat. No. 4,362,757 to Chen, et al. a crystallized sugar product and a method of preparing same are described. The method disclosed in the Chen, et al. '757 reference includes concentrating sugar syrups to a solids content of about 95% to about 98% by heating to a temperature of about 255° F. to about 300° F. The resulting concentrated syrup is maintained at a temperature not less than about 240° F. in order to prevent premature crystallization. A premix consisting of an active ingredient (e.g., a volatile flavor, an enzyme, an acidic substance such as ascorbic acid, a fruit juice concentrate, or a high invert sugar substance) is mixed with the concentrated sugar syrup. The combination is subjected to impact heating until a crystallized sugar product made up of fondant-size sucrose crystals and the active ingredient is formed which has a moisture content of less than 2.5% by weight. The Chen, et al. '757 process requires heat intensive concentrating and heating for nucleation.

A similar procedure is disclosed in U.S. Pat. No. 4,338,350 to Chen, et al. wherein a process for preparing a crystallized sugar product containing a food ingredient is described. The Chen, et al. '350 disclosure calls for concentrating a sugar syrup at a temperature range of about 250° F. to about 300° F. to a solids content of about 90 to 98% by weight. A food ingredient, such as gelatin, cocoa powder, pectin concentrate, etc., is admixed with the sugar syrup. The mixture is subjected to impact beating until a crystallized sugar product made up of aggregates of fondant-size sucrose crystals and food ingredients is formed. The Chen, et al. '350 process requires heat intensive concentrating and beating to induce crystallization.

U.S. Pat. No. 3,365,331 to Miller, U.S. Pat. No. 4,338,350 and U.S. Pat. No. 4,362,757 describe a process for crystallizing sugar, which involves impact beating a sugar solution to provide nucleation. The process involves input of considerable amount of energy and has problems directly related to temperature control.

Other disclosures include British Patent Specification No. 1 460 614 and U.S. Pat. No. 3,972,725 (Tate & Lyle Limited) which disclose a continuous process wherein a syrup solution is catastrophically nucleated and discharged into a crystallization zone. Catastrophic nucleation is achieved by subjecting the solution to shear force which can be applied in apparatus such as a colloid mill or homogenizer. The solution is discharged onto a moving band where the water must be boiled off by maintaining the material at a relatively high temperature. A related process has been disclosed in British Patent Specification 2 070 015 B and U.S. Pat. No. 4,342,603, which is used for crystallization of glucose. In the disclosed procedure, a supersaturated solution is subjected to shear force and allowed to crystallize on a belt. Both the sucrose process and the glucose process require solution processing at high temperatures and are, consequently, energy intensive.

U.S. Pat. No. 3,197,338 to Hurst, et al. discloses a process for crystallizing glucose which includes kneading a glucose solution to induce nucleation followed by crystallization to form a solid glass which is then ground. Another glucose crystallization process has been disclosed in GB 2 077 270 B in which starch hydrolyzate is concentrated by evaporation and then simultaneously crushed and mixed during crystallization while cooling. The product is further milled. These processes also require nucleating by beating a solution which includes glucose.

UK Patent Specification G B 2 155 934 B of Shukla, et al. discloses a method for crystallizing sucrose or glucose from a solution. Shukla, et al. subject a sugar solution to evaporation to produce a supersaturated sugar solution. The supersaturated solution is then subjected to shear in a continuous screw extruder to induce nucleation. The retention time of the syrup is below 25 seconds (on the average) at a temperature of 115° C. to 145° C. (239° F.–293° F.) for sucrose and 100° C.–135° C. (215° F.–275° F.) for glucose. After the syrup is subjected to progressive nucleation, Shukla, et al. pass the syrup onto a moving band to permit crystallization to continue at a gradual rate at relatively high temperature. The Shukla, et al. process requires maintenance of the solution at temperatures which do not drop below the boiling point of water.

Additional technology has been developed which relates to processing food and food ingredients. For example, a series of U.S. patents issued to Thomas E. Chivers (U.S. Pat. No. 3,762,846, U.S. Pat. No. 3,723,134, and U.S. Pat. No. 3,557,717) disclose a solution process for making candy floss from a cooked slurry or syrup. The ingredients are blended and heated at a first temperature, e.g., 200°–205° F. (93°–96° C.), to form a slurry. After forming the slurry, the batch is cooked or boiled at a substantially higher temperature, e.g., about 340° F. (171.1° C.), and thereafter discharged through an atomizing nozzle. Most of the moisture contained in the molten candy flashes off as it is discharged. The Chivers disclosures rely on dissolution of the ingredients, e.g., sugar and other ingredients, in water and then heating extensively to drive the water from the solution. Most of the water is driven off after discharging the solution. Thus, the Chivers technology suffers from drawbacks associated with sustained high temperature processing and dissolution of ingredients during processing.

Another method for process material is disclosed in European Patent Application 0 387 950 A1 of Stork. The Stork process is a method of preparing a foam spray-dried product by collision of a stream of gas which contains dry particulate material, with a jet of droplets of a liquid solution. A liquid solution which contains at least one of the ingredients of the end product is combined with gas and heated before spraying as a jet of droplets for collision with the dry particulate. The Stork system is designed to process a low density product; it requires an elaborate equipment arrangement, and is energy intensive.

In U.S. Pat. No. 3,615,671 to Shoaf discloses a method of producing food products by encasing dry particulate food particles within a casing of spun sugar filaments. In order to enhance 1) shaping of the fibers and particles and 2) the tendency of the fibers to stick to each other with a minimum of compression, Shoaf uses a humectant in the sugar mix to be spun and controls the relative humidity of the gases surrounding the filaments as they are spun. The humectants described as useful are as follows: invert syrup or corn syrups and polyhydric alcohols, e.g., sorbitol, glycerol and pentahydric alcohols, e.g., xylitol. Shoaf is concerned with preventing crystallization of the spun sugar in order to enable the manufacturer to encase dry food particles by wrapping and compressing filaments of the spun sugar around the particles.

More recently, a trade brochure provided by Domino Sugar Corporation, Industrial Products, entitled "Co-Crystallization" (undated) describes a product in which micro-sized crystals form aggregates having a second ingredient disposed over the surface of each aggregate. The process for producing this new product requires that all starting materials must be in a liquid state. Therefore, solvent must be driven off by heat and/or vacuum in order to concentrate the syrup from crystalline growth. As in other solution process energy is required to transform the sugar to microsized crystals.

Inherent in the procedures set forth above, as well as other procedures known in the art, is the technical philosophy of dehydration to promote crystallization. Supersaturation, pan drying, and nucleation by agitation or chemical reaction depend on the principle of eliminating water to form crystals. A common difficulty with crystallization based on this technical underpinning has been lack of control over crystalline growth.

Thus, it would be significant advance in the art of crystallization, to provide a mechanism for crystal formation which departs from traditional dehydration, and which provide a low energy means for producing a crystalline sugar product.

Accordingly, it is an object of the present invention to enable the artisan to make a sugar product which has a predictable crystalline growth and uniform crystal size without energy-intensive procedures. Other objects and surprising new sugar-crystal technology are disclosed in the remainder of the Specification.

SUMMARY OF THE INVENTION

The present invention is a new form of crystalline sugar as well as a method of making same. The new crystalline sugar results from a unique crystallization process which involves transformation of an amorphous shearform sugar mass to a new crystalline sugar. The transformation includes forming a bi-dimensionally stabilized sugar crystalline frame from an outer portion of the amorphous shearform mass followed by converting the remaining portion of the mass to a substantially completely crystalline structure which retains the cross-sectional dimension of the sugar crystalline frame. Preferably amorphous shearform masses, which are discussed more fully hereinafter, are produced in the shape of elongated needles (or rods when magnified). Each rod has a linear dimension and a defined cross-sectional dimension, which is in a plane intersecting the linear dimension at a right angle. The amorphous mass is continuous throughout the length and cross-section of each rod. Therefore, each rod has an outer portion which forms the surface of the rod and a remaining portion which is the amorphous mass within the body of each rod. Thus, the new process and product consists of a crystalline frame first formed from the outer portion and a completely crystalline structure built thereon by conversion of the remaining portion of the amorphous mass to crystalline form, such that the cross-sectional dimension of the resulting structure is substantially the same as the originally-formed frame. Key to the present process is the formation and maintenance of a bi-dimensionally stable structure.

The bi-dimensional stability is achieved by initially establishing the crystalline frame and ensuring that conditions are controlled to maintain the frame during conversion. This can be accomplished by contacting shearform amorphous sugar with water in a substantially non-aqueous gaseous environment at a rate and in an amount which crystallizes amorphous sugar on the outer portion of the mass. Subsequently, conversion is accomplished by continued controlled contact of the shearform amorphous mass with water at a rate and in an amount which maintains the shell and permits the remaining portion of the mass to crystallize.

An alternative procedure includes controlledly adding heat to an amorphous shearform sugar mass in a substantially non-aqueous gaseous environment which has a controlled relative humidity (r.h.) until amorphous sugar on the outer surface of the mass forms a shell having a fixed cross-sectional dimension. Heat is continually added in a controlled amount sufficient to maintain the shell and convert the remaining mass of amorphous sugar to the crystalline structure. It is noted that heat can be controlledly added by 1) increasing the temperature of the environment where the transformation takes place, 2) maintaining a constant temperature, or even 3) allowing the temperature to decrease at a rate which causes heat to transfer to the mass.

Preferably, the stabilized bi-dimensional structure has a cross section which is both monodispersed and which is microcrystalline, i.e., not greater than about 50 μm, preferably not more than about 40 μm, and, in a most preferred embodiment, not more than about 10 μm.

Contrary to teachings in the art of sugar crystallization, the new sugar product is prepared in accordance with the present invention by adding water to amorphous sugar. Amorphous sugar as used herein means a sugar stock which contains a high percentage of amorphism, i.e., greater than 50% by weight, and preferably greater than 70% by weight of the sugar stock is amorphous. The unique procedure of this invention includes contacting amorphous shearform sugar with a substantially non-aqueous gaseous environment with a controlled amount of water at a rate and in an amount which initially stabilizes the structure of the sugar in two dimensions.

While the present invention primarily concerns sugars as defined herein, it is also intended to include processing (and products therefrom) an amorphous solid form of a solvent-soluble compound which is capable of forming crystals. Preferably, the solvent for the process and product(s) herein is water.

Amorphous sugar can be provided by shearform processing a sugar-containing feedstock. The shearform process according to the present invention is one in which a feedstock is subjected to shear and heat simultaneously in order to obtain flash flow. One shearform process includes subjecting a feedstock containing sugar to shear created by high speed spinning on a spinning head. The spinning head casts the material outwardly as the feedstock undergoes flash flow. Flash flow is created as a consequence of simultaneous application of heat and shear. An alternative shearform process includes heating a non-solubilized feedstock having a sugar carrier sufficiently to provide internal flow. The feedstock is ejected while the sugar possesses internal flow, and is then subjected to disruptive fluid shear force to form multiple masses of carrier. Other methods are contemplated which provide the same critical conditions of heat and shear wherein a substantially solid feedstock containing sugar can be transformed physically and/or chemically from a solid structure to an essentially amorphous solid structure.

An additive can be included in the amorphous sugar and become part of the resulting product. This is referred to herein as co-crystallization. When such an additive is provided, it is included without reducing the amorphism of the sugar and without deteriorating the resulting crystalline structure. Additives contemplated for use herein include, but are not limited to, flavorants, bio-affecting agents, dyes, fragrances, food products, food ingredients, and other compatible agents. Flavorants in the present invention includes sweeteners of all types, natural and synthetic.

In one preferred embodiment of the present invention, the shearform product can be subjected to air as the gas at a temperature of at least about 50° C. The amount of water in the air is controlled to achieve localized crystallization on the surface of the shearform sugar product. In a one embodiment that is accomplished in a closed system where the initial humidity of the air is not greater than 50% relative humidity and preferably between 5% and 30% relative humidity.

Another aspect of the present invention includes the use of a crystallization modifier which enhances the formation of a crystalline frame and the conversion of the remaining mass. Enhancement as used with respect to the process of the present invention principally means acceleration of the process. Enhancement also includes contribution to the strength of the crystalline structure, and predictability of results. Other benefits such as reduced-size product also is achieved by use of crystallization modifiers.

Crystallization modifiers, which are preferably added to sugars before being processed to amorphous shearform mass (or can be coated on the sugar), are used to affect the rate of crystallization. Water itself is a crystallization modifier, and is preferably included in the amorphous shearform sugar mass in an amount of between about 0.5% to about 2.0%. Non-saccharide hydrophilic organic materials (NSHMs) are also used as crystallization modifiers. Even though some NSHMs are surfactants, other materials can be used. Materials found to be most effective have a hydrophilic to lipid balance (HLB) of 6 or greater, i.e., they have the same degree of hydrophilicity as surfactants characterized by degree of HLB. Such materials include, but are not limited to anionic, cationic, zwitterionic surfactants as well as neutral materials which have an HLB of six (6) or greater. Preferred NSHMs are hydrophilic materials having polyethylene oxide linkages. Also, the preferred NSHM's have a molecular weight of at least 200 and preferably at least 400.

Polyoxyethylenes and polyethylene glycols are preferred crystallization modifiers in the present invention. In one embodiment the NSHM crystallization modifiers are included in feedstock in an amount of from 0.1 up to 20% by weight and preferably in an amount of from 0.1 to 5% by weight. The NSHM crystallization modifier can also be coated on the shearform product. Surface active agents useful as crystallization modifiers includes but are not limited to, the Spans™, Tweens™, (which are commercially available from ICI Americas Inc.) and Lecithins having an HLB greater than 6. Carbowax™ is yet another crystallization modifier which is very useful in the present invention.

As a result of using crystallization modifiers as set forth above, the process for converting the amorphous sugar mass is significantly enhanced. The gas which can be air, can be maintained at a temperature of between about 40° C. and about 70° C. This wide range is especially useful in adapting to environments around the world. Moreover, the contacting with water required to attain the transformation of the present invention can be achieved by using a gas having relative humidity of between 5% and 90%. Once again, this is a significantly broadened range which results from the use of crystallization modifiers in the shearform amorphous mass.

By use of a NHSM crystallization modifier the process and product of the present invention can be reproduced with a high degree of predictability. As additional crystallization modifiers which enhance the procedure and product of the present invention are identified, Applicants intend to include all such additional crystallization modifiers within the scope of the invention claimed herein.

As a result of the present invention, a new crystalline form has been provided. This crystalline form has been found to be useful in products which require a uniform crystal sugar product. For example, a new fondant consisting of substantially crystalline sugar product of the present invention can be prepared. The resulting product is smooth and flowable, and has a new microscopic composition which is different from any known fondant product.

The nature of the process of the present invention enables the artisan to make crystalline product of a particular size and shape with a high degree of predictability. Reduced size crystals can be effectively produced without the need of energy intensive grinding and sieving. This is a significant departure from crystalline products and processes of the past.

As a result of the present invention a new fat and mimetic ingredient is also provided for use in foods, e.g., fondants, frosting, fillers for baked goods—especially cookie fillers, etc.

Moreover, the present invention can be used in tableting. Active agents can be incorporated with the product or in the product itself through co-crystallization and tableting. The tablet can be prepared with or without the use of an excipient. Alternatively, the product of the present invention can be used in the role of a tablet excipient.

The present invention has uniquely harnessed the natural drive of matter to seek and maintain a lower energy state, to create a process for controlled crystalline growth as well as a new product resulting therefrom. Material which has a natural crystalline structure in its lowest entropy state is transformed to an increased entropy state where it is amorphous. In the amorphous condition the material possesses a natural tendency to obtain a lower energy state—i.e., the crystalline form of the material. The inventors herein have harnessed this natural tendency of matter to drive controlled crystallization. This has been achieved by providing an essentially non-solvent system in which a controlled amount of solvent has been made available to permit controlled crystallization. The variety of procedures and products resulting from harnessing of natures tendency to seek its lowest entropy state are boundless, and the present claims cover any procedure which utilize the principal set forth herein.

While not wishing to be constrained by theory, it is presently believed that the unique crystallization is achieved by a novel processing approach which relates to the glass transition temperature of the sugar. In particular, the glass transition temperature ($T_g$) can be approached in a process sense by raising the heat to approach the $T_g$ of the amorphous sugar/water/crystallization modifier composite. Alternatively, the $T_g$ of the sugar/water/crystallization modifier composition can be lowered by adding water via humidity to depress the $T_g$ to the ambient temperature so that localized crystallization can occur to obtain the stabilized crystalline framework. Understanding of these principles appears to enable the artisan to vary the parameters to artisan the unique process and product therein.

For a better understanding of the present invention, references made to the drawings, the following detailed description and non-limiting examples. The scope of the invention is described in the claims which follow the detailed description.

BRIEF DESCRIPTION OF THE DRAWINGS

FIG. 4 is an artist-rendered schematic of shearform amorphous sugar prior to bi-dimensional stabilization and subsequent crystalline growth;

FIG. 5 is an artist's rendition of a bi-dimensionally stabilized shearform product as the crystalline growth occurs;

FIG. 6 is a artist's rendition of a schematic representation of a linear cross section of the product shown in FIGS. 1–3; and FIG. 7 is a graph depicting crystallization as a function of time and moisture in a shearform product.

DETAILED DESCRIPTION OF THE INVENTION

The present invention is a new crystalline sugar which is produced by first stabilizing an amorphous shearform sugar mass in two dimensions, preferably such that the dimension of the cross section established in the plane of the two dimensions is monodispersed. Subsequent crystalline growth occurs whereby the remainder of the amorphous mass crystallizes against the frame formed by the initial crystallization so that the cross-sectional dimension of the resulting structure is the same as the cross-sectional dimension of the frame.

Figure 1A:
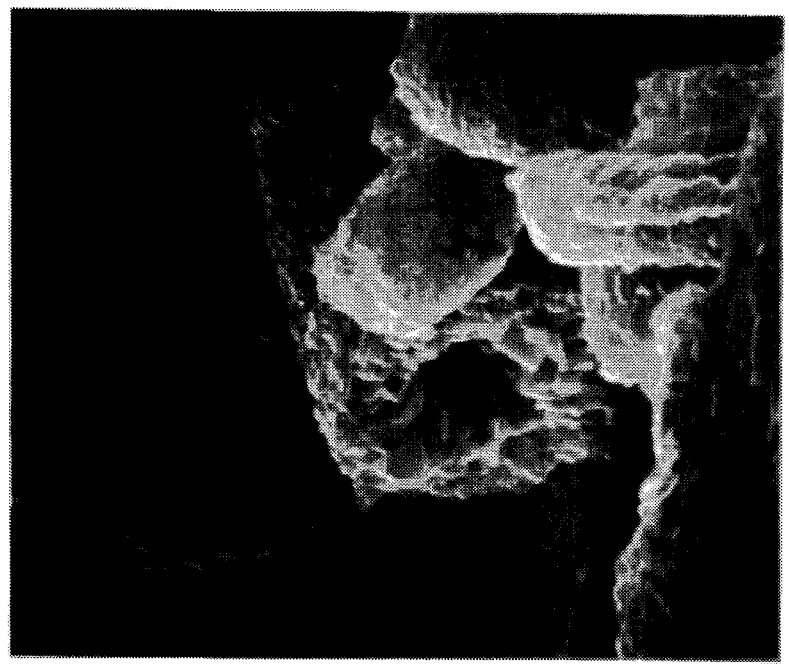
FIGS. 1A, 1B, and 1C are photomicrographs taken at 3000, 2900, and 2490 magnification, respectively, of the unique crystalline sugar product of the present invention.
Figure 1C:
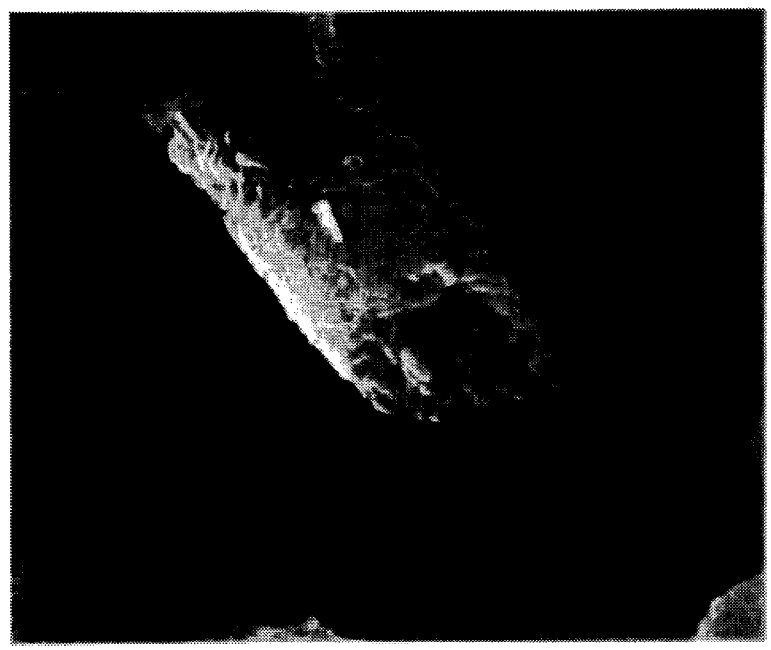
Figure 1B:
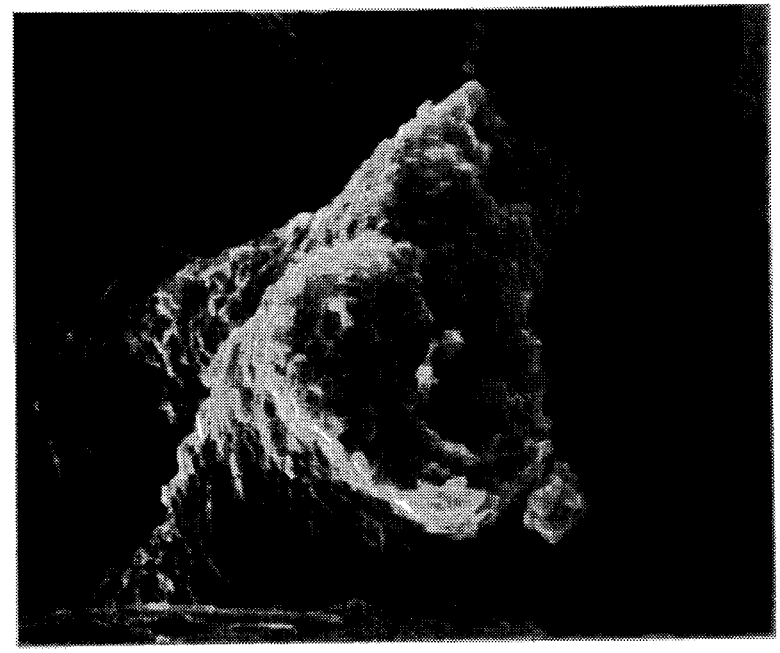
Figure 2B:
FIGS. 2A, 2B, 2C, and 2D are photomicrographs of shearform amorphous sugar masses taken at 500 magnification for 2A and B, and at 2000 magnification for 2C and D.
Figure 2A:
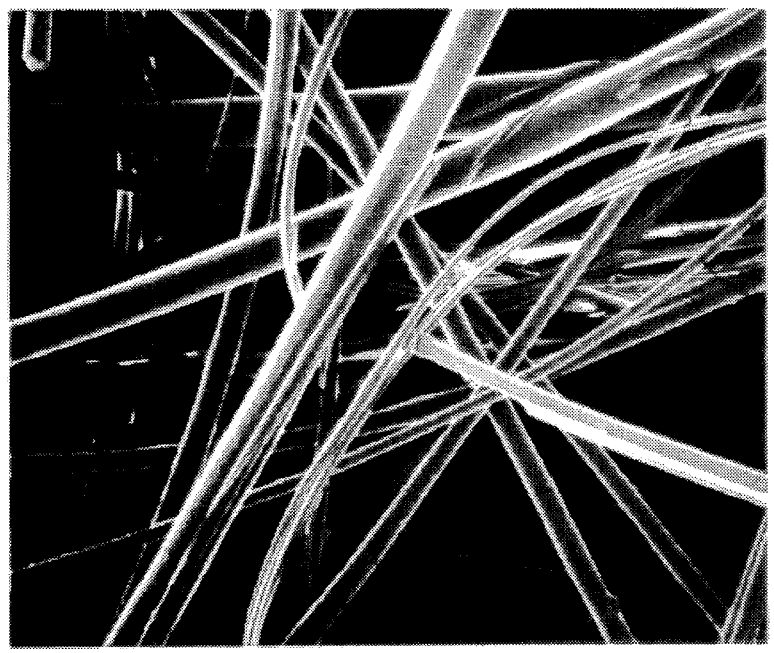
Figure 2D:
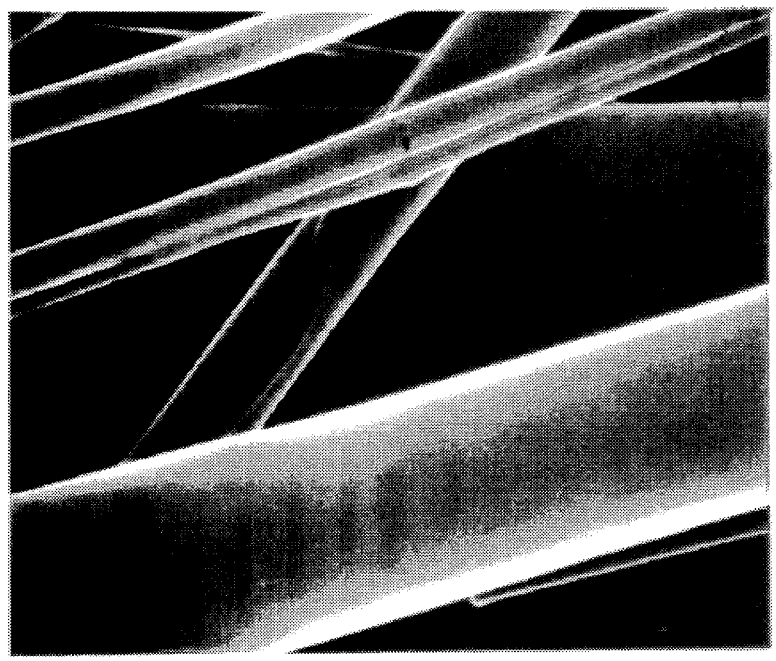
Figure 2C:
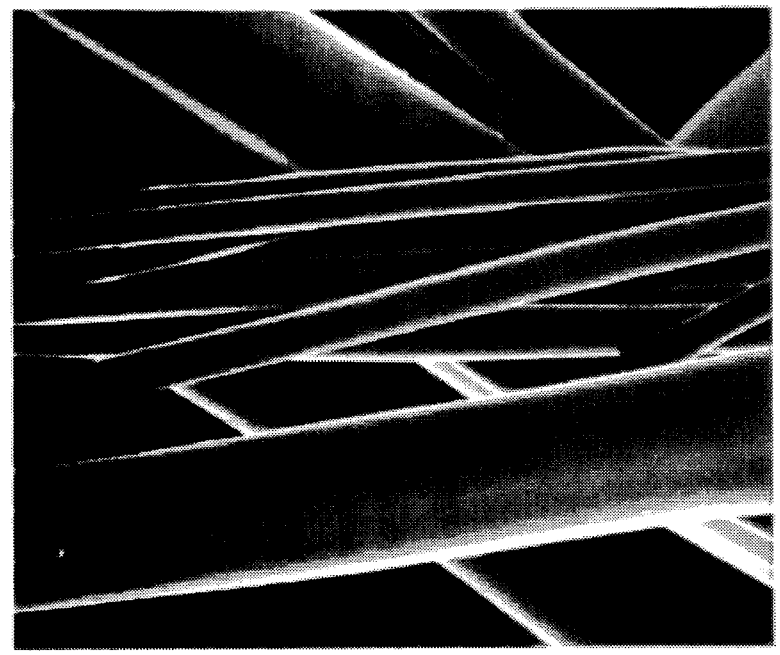

FIGS. 1A through 1C and FIG. 3 are photomicrographs which depict the product of the present invention. Bi-dimensionally stabilized sugar is shown which has been subsequently crystallized to retain the cross-sectional dimension of the original frame. FIGS. 1A–1C show space created at the interior of each of the fibers as a result of amorphous sugar mass crystallizing against the framework. Since crystallized sugar molecules are ordered as compared to amorphous sugar molecules, crystallized sugar occupies less space. Therefore, once the crystalline frame is formed subsequent crystallization of amorphous sugar against the frame creates a void or space in the interior of the rod.

Figure 3:
FIG. 3 is a photomicrograph of crystalline sugar prepared by the process herein, but with added vegetable oils to demonstrate the pattern of crystallinity in the structure.

In FIG. 3, a sample is depicted which included 50% vegetable oil. Vegetable oil was included to shown crystallization as darkened areas under the microscope. Dark areas of the rods show where crystallization has occurred, e.g., along the outside of the length of each of rods as well as through the interior of each of the rods. A detailed description of how this occurs has been set forth hereinbelow. FIG. 3 is a photomicrograph of the sugar crystalline product of the present invention taken at a magnification of 40×.

The present invention concerns the transformation of sugar from amorphous to crystalline condition without the use of conventional high energy procedures. In the present invention amorphous sugar is first formed from "sugars." "Sugars" are those substances which are based on simple crystalline mono- and di-saccharide sugars, i.e, based on $C_5$ and $C_6$ sugar structures. "Sugars" include sucrose, fructose, mannose, pentose, xylose, ribose, lactose, arabinose, maltose, isomalt (e.g., Palatinit® Type PF made available by S üBungsmittel GmbH, Mangheim, Germany), sugar alcohols such as sorbitol, xylitol, mannitol, maltitol, etc. The choice of sugar in the present invention is sucrose.

A shearform sugar product is used in the technique of the present invention to obtain the new sugar product. A shearform sugar product is a substantially amorphous sugar which results from subjecting sugar to heat and shear sufficient to transform crystalline (usually granulated) sugar to amorphous sugar without the use of a solution. Thus, in the sense of the present invention, a shearform sugar product is characterized as a sugar product resulting from a non-solubilized sugar. It is the starting material for forming the unique crystalline product of the present invention.

In the preferred embodiment of the present invention amorphous shearform masses are fibers which appear as rods under magnification. FIGS. 2A–2D depict the preferred shearform starting material of the present invention. As a most preferred embodiment, amorphous shearform starting material also includes crystallization modifiers. The modifiers, eg., Carbowax™, Spans™, Tweens™, lecithin etc., can be included in the feedstock used to made the shearform material, or coated on the shearform material before crystallizing.

The process of the present invention is unique in that it employs a procedure which is directly opposite the classic teaching of sugar technology to form a crystal by concentration and/or supersaturating sugar from a solution. In fact, the present invention employs a procedure which requires controlled contact of a sugar solvent, preferably water. Water is controlledly added to amorphous sugar to initiate and promulgate the unique crystalline growth claimed and disclosed herein.

This entire concept is directly contrary to the prior art which specifically teaches the artisan to crystalize sugar by eliminating or dehydrating solvent by driving it off with heat and/or vacuum.

Specifically, the present invention utilizes shearform amorphous sugar which has been produced by processing the sugar under conditions such as those found in cotton candy machines. In these machines, sugar is introduced to a spinner head in which it is subjected to heat and shear created by centrifugal force from the spinning head. Disclosures which relate to spinning substances include U.S. Pat. No. 4,855,326, U.S. Pat. No. 4,873,085, U.S. Pat. No. 5,034,421, U.S. Pat. No. 4,997,856, and U.S. Pat. No. 5,028,632.

Examples in the U.S. patents listed above describe processing feedstock material by subjecting it to high speed spinning on a spinning head in which the substance is also subjected to heat by a heating element. The change of temperature is quite large, which is believed to be occasioned by the spinning head quickly and efficiently spreading the feedstock material against the heating element circumferentially disposed around the perimeter of the spinning head. Thus, extensive surface contact of the feedstock against the heating element is provided. An additive can be included in the feedstock so that co-crystallization results when processed according to the present invention.

More recently, commonly owned co-pending application entitled "Process For Making Shearform Matrix," filed on Oct. 23, 1992 and assigned U.S. application Ser. No. 965,804, discloses another process for making shearform matrix by subjecting non-solubilized feedstock to heat sufficient to induce internal flow, ejecting a stream of the feedstock while possessing internal flow, and then subjecting it to disruptive fluid shear force which separates it into separate parts or masses having transformed morphology. The product is amorphous. Other ingredients can be included in the material so that when it is used in the present invention, co-crystallization will occur.

The amorphous shearform product produced as set forth above, with or without the additive, is then contacted with a substantially nonaqueous gaseous environment, e.g., air, and a controlled amount of solvent, such as water. The purpose of contacting the shearform sugar product with water in the substantially nonaqueous environment is to permit crystallization of the sugar without collapse of the structure of the shearform amorphous sugar. Once the outside portion is crystallized to form a shell or frame of the structure, the remaining portion of amorphous mass can be crystallized (preferably at a faster rate) to achieve a fully crystalline sugar structure.

Preferably, the shearform amorphous sugar is held at a temperature close to or just below its glass transaction temperature. It is believed that as water enters the mass the glass transition temperature is lowered to allow localized crystallization to occur to form an outer shell or frame. The frame provides the rigidity of the structure so that the cross-sectional dimension is maintained during crystallization of the remainder of the structure. If solvent, e.g., water, is permitted to be exposed too rapidly to the site of crystallization, the structure degrades and tends to collapse on itself, resulting in globules of saturated sugar crystals.

The inventors have discovered by controlling the environment where crystallization is occurring, they are able to dimensionally stabilize the shearform product, which is usually in the form of fibers (or rods under magnification), in two dimensions. By two dimensions is meant two dimensions within the structure of the product. Thus, referring to FIG. 5, the controlled contact with moisture in the nonaqueous gaseous environment stabilizes the shearform product in the x and y direction. This stabilization occurs along the entire length of the rod R.

By continued controlled crystallization in the substantially nonaqueous gaseous environment, conversion of the amorphous mass continues until it is transformed into a substantially all crystalline structure. The transformed rod may bend or have a slightly serpentine configuration, but it retains the same cross-sectional dimension as the crystalline frame.

Inasmuch as the structure of the rod R has been bi-dimensionally stabilized, crystallization causes the molecules present in the sugar mass to occupy less space. Amorphous sugar contains free volume space which is space between amorphous sugar molecules. Consequently, amorphous sugar appears as a continuous mass in FIG. 4. As the sugar crystallizes, free volume space is eliminated and the solid sugar structure occupies less space.

Therefore, the mass of sugar within the rod R contracts toward the outer surface of the rod. See FIG. 5. At present, a typical crystallization according to the present invention forms a passage which is somewhat discontinuous. An artist's representation of the product depicted is shown in FIG. 4 in longitudinal cross-section. There are some portions of the rod where the passage is interrupted or discontinuous. These discontinuities are represented as interior cross sections D.

Furthermore, the present invention also includes the concept of providing a highly controlled formation of crystals. A crystal produced with such a high degree of specificity as to size is referred to herein as "monodispersed." However, the monodispersed aspect of the present invention has to do with the bi-dimensional stabilization. In FIGS. 4, 5, and 6, a dimension L is shown which is referred to herein as the crystal diameter. It is the longest straight line distance in the cross-sectional plain P through the crystal. "Monodispersed" as used herein means that at least about 60% by weight, preferably at least 80 and most preferably at least 90%, of the crystals have a diameter which is within 60% of the mean crystal diameter.

In yet a further embodiment, the crystals are bi-dimensionally monodispersedly stabilized with at least 60% of the crystals being within 50% of the mean crystal diameter, and in a most preferred embodiment within 40% of the mean crystal diameter.

In order to effect the unique crystallization where the amorphous sugar contains a crystallization modifier such as 0.1% to 5% of a polyoxyethylene, a polyethylene glycol or a Carbowax™ and a product resulting therefrom, water is made available in the case of sucrose by providing an environment having at least about 5% relative humidity, and preferably between about 10% r.h. and 70% r.h., at a temperature of from about 35° C. to about 60° C. and preferably 40° C. to about 55° C.

A highly preferred embodiment of the present invention includes the use of a NHSM crystallization modifier. The crystallization modifier can be added during the preparation of the amorphous shearform product, or coated on the shearform product before crystallizing. It has been found that by addition of the NHSM crystallization modifier, the time frame for crystallization can be accelerated from days (up to about 30 days) to about three (3) minutes.

It is believed that crystallization modifiers, such as non-saccharide hydrophilic organic materials (NSHMs), compete with the amorphous sugar for water. This phenomenon lowers the glass transition temperature of the sugar in localized regions of the shearform mass. Consequently, regional crystallization occurs to form an outer shell or frame. The frame provides a rigid skeleton against which conversion of the remaining amorphous sugar mass occurs. It appears that the crystallization modifier creates free volume space in the molecular arrangement of the amorphous sugar, which, in turn, accelerates the inventive process of crystalline-framing and structurally-integral-conversion.

By using NSHM's the time for inventive crystallization has been reduced from days to several hours and to several minutes. This ability to accelerate the unique crystalline growth of the present invention, is believed to enhance significantly the commercial use of the invention. The present invention covers the use of all crystallization modifiers which enhance crystalline growth in the context of the present invention.

A further aspect of the present invention is co-crystallization. Any compatible additive can be included internally in the crystal structure of the present invention so that the end product includes the additive(s). Such additives can be selected from the group consisting of flavorants, bio-affecting agents, dyes, fragrances, food products, food ingredients, and other agents which are compatible. Compatible means the additives can be included in the amorphous sugar without destroying the amorphism, and can be included in the crystalline product without deteriorating the structure thereof.

A non-limiting list of bio-affecting agents is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, physchotropics, antimanics, stimulants, gastrointestinal agents, sedatives, antidiarrheal preparations, anti-anginal drugs, vasodiaIators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper-and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

The present invention is particularly useful in providing a new delivery system for inhalants. Inhalants must be formed of minute particles which are rapidly absorbed by the patient. Thus, since sugar is quickly dissolved at body temperature, inhalants co-crystallized with the unique tiny highly-uniform product of the present invention can be easily delivered as a tiny particulate which is rapidly absorbed by the body. In another aspect of this invention, the shearform sugar is compacted sufficiently to form a porous compacted mass. The matrix is then subjected to controlled heat and water to bi-dimensionally stabilize the sugar and form a crystalline matrix. The matrix can then be treated with a saturated aqueous sugar solution to deposit more sugar on the crystalline structure within the matrix to add additional rigidity to the matrix structure. Preferably the supersaturated solution is an ethanol/water sugar solution and preferably the water content is less than 5%. Rapidly dissolving wafers can be made by this process. Various bioeffecting agents, flavors, taste masking ingredients and the like can be deposited within the matrix either before or after the step of processing with the saturated sugar solution.

EXAMPLES

In the following examples, the shearform amorphous starting material was prepared by spinning granulated sucrose (and any other material indicated within the example) in a "cotton candy" fabricating type equipment.

Example 1

Experiments were first conducted to determine the effect of moisture within the shearform product on the resulting crystallization. Two samples were prepared, both of which consisted of approximately 100 grams of granulated sucrose and about 10 grams of tap water. The material was allowed to set for about 12 hours and then spun on candy cotton type equipment. The resulting amorphous matrix was analyzed to determine the percent of water present in the shearform product. One example, Example A included 1.36% water. Example B showed a percent of water at 0.91%.

Examples A and B were each placed in 32 oz. glass containers and sealed. The ambient air inside each container was about 40% relative humidity (r.h.). The sealed containers were maintained at 63° C. for a period of 30 days. In each case the amount of moisture remained constant as the temperature was raised to 63° C. In each sample crystallization proceeded by first forming a crystalline frame followed by converting the remainder of the mass where retaining the cross-sectional dimension of the frame. The samples exhibited crystallization as shown in FIG. 3.

The results of crystallization are shown in FIG. 5. Thus, after 25 days nearly all of the shearform product containing 1.36% water at the inception of crystallization was crystallized. About 50% of the product containing 0.91% water was crystallized after 25 days. Apparently sample A had sufficient water to achieve crystallization at a faster rate.

In both cases, however, analysis of the crystalline product revealed that a highly uniform, monodispersedly, bi-dimensionally-stabilized crystalline product had formed with continued crystallization in the third dimension. The mean cross sectional dimension of the product was about 10 μm. The product prepared in accordance with these examples was very useful in preparation of a fondant.

SURFACTANT EXAMPLES

In these examples experiments were conducted to determine the effect of surface active agents as crystallization modifiers on the procedure and the product of the present invention. The shearform product used in these examples was prepared on a cotton candy type machine in which the feedstock was spun at a temperature of about 160° C. and about 3600 rpm.

Span 80™/Tween 80™- HLB 8.0

A first example was prepared using a composition of 99% sucrose and a surfactant combination of 65% Span 80™ and 35% Tween 80™. The surface active agent had a HLB of 8.0. The composition was spun. The resulting shearform product was compact and possessed some fluffiness. Crystallization started to occur within several hours and was completed between 12 and 24 hours. The product was crystallized to provide the unique structure of the present invention.

Span 80™/Tween 80™- HLB 10.0

A second surfactant example was run using a combination of 46.7% Span 80™ and 53.3% Tween 80™ which resulted in an HLB of 10. The feedstock consisted of 99% sucrose and 1% of the surfactant combination.

The mixture was spun and subjected to the same conditions as in the previous surfactant examples. The resulting floss was very soft and contained tufts. The product was exposed to air at a temperature of about 21° C. and at a relative humidity of about 40%. Crystallization started to occur within several hours, and was complete well within 24 hours. Once again, a remarkable acceleration occurred as a result of using the surfactants in the proportions set forth above.

Span 80™/Tween 80™- HLB 12.0

In a third surfactant example, the feedstock included 99% sucrose and 1% surfactant combination which included 28% Span 80™ and 72% Tween 80™. The HLB was 12.0.

The composition was processed as in the proceeding examples resulting in a very soft floss.

Very nice crystallization was completed within 24 hours.

Tween 80™- HLB 15.0

A fourth surfactant example was prepared with a composition of 99% granulated sucrose and 1% of Tween 80™. The composition was processed as in the previous examples producing a very nice floss and crystallization within several hours. As before, the crystallization was completed within 24 hours.

COMPARATIVE SURFACTANT EXAMPLE

Span 80™- HLB 4.3

In a comparative surfactant example, a composition of 99% granulated sucrose and 1% Span 80 (having an HLB, high to low lipid balance, of 4.3), was spun. The combination was blended until well mixed and then processed in the spinning head.

The spun product appeared as a very soft, wispy floss which was light in color. After several hours of exposure to a gaseous environment having a relative humidity of about 40% r.h., the floss began to collapse. Within 24 hours, the entire mass had, in fact, hardened to a rigid disc. Thus, the surface active agent having an HLB of less than 6.0, i.e., 4.3, failed to provide the carefully crystallized structure of the present invention.

In summation, therefore, it can be seen that the use of the surface active agent in the process of the present invention can result in an accelerated crystallization. This could significantly improve commercial utilization of the present invention.

COMMERCIAL EXAMPLE

In order to demonstrate the commercial value of the present invention, a sample of amorphous shearform material was prepared using Carbowax™ as a crystallization modifier. The Carbowax™ was included in granulated sucrose to provide a feedstock for spinning a shearform material. The shearform material was taken immediately from the spinning process and introduced to a rolling mill in order to reduce impurities in the form of unspun spheres. The product was immediately introduced to hot humid air whereby crystallization occurred in the form specified herein, i.e., frame formation followed by conversion of the remainder of the amorphous mass without collapse of the crystallized frame. The transformation amazingly occurred within only three minutes.

This is an excellent result for use of the present invention in a commercial setting. Industrial production of the unique crystalline product of the present invention has many applications.

Thus, while there have been described what are presently believed to be the preferred embodiments of the present invention those skilled in the art will appreciate that other and further modifications can be made to the present invention without departing from the true spirit thereof, and it is intended to include all such further embodiments as come within the scope of the invention set forth in the embedded claims.

What is claimed is:

1. A method of forming a crystalline sugar product comprising:

forming a bi-dimensionally stabilized sugar crystalline frame from an outer portion of a shearform amorphous sugar mass, said bi-dimensionally stabilized frame having a linear dimension and a cross-sectional dimension, and converting the remaining portion of said mass to a substantially completely crystalline structure which substantially retains said cross-sectional dimension of said bi-dimensionally stabilized sugar crystalline frame.

2. The method of claim 1 wherein said forming comprises:

controlledly contacting said shearform amorphous sugar mass with water in a substantially non-aqueous gaseous environment at a rate and in an amount sufficient to crystallize amorphous sugar on the outer surface of said mass to form a shell having said cross-sectional dimension.

3. The method of claim 2 wherein said converting comprises:

continued controlled contacting of said shearform amorphous sugar mass having said shell formed thereon with water in said environment at a rate and in an amount sufficient to maintain said shell and permit said remaining portion of said mass to crystallize to form said crystalline structure.

4. The method of claim 2 wherein gas in said substantially non-aqueous gaseous environment is air maintained at a temperature of at least about 50° C. while said amorphous sugar mass in the presence of a controlled amount of water which initiates crystallization of amorphous sugar is contacted with said water.

5. The method of claim 2 wherein said substantially non-aqueous gaseous environment is maintained at a relative humidity (r.h.) of not greater than about 50% in an amount sufficient to effect said crystallization.

6. The method of claim 5 wherein said relative humidity is between about 5% and 50%.

7. The method of claim 1 wherein said forming comprises:

controlledly adding heat to said shearform sugar mass in a substantially non-aqueous gaseous environment which contains a quantity of water sufficient to transform amorphous sugar on the outer surface of said mass to a shell having said cross-sectional dimension.

8. The method of claim 7 wherein said converting comprises:

continued controlled addition of heat to said shearform sugar mass having said shell formed thereon in said environment at a rate and in an amount sufficient to maintain said shell and permit said remaining portion of said mass to crystallize to form said crystalline structure.

9. The method of claim 7 wherein gas in said substantially non-aqueous gaseous environment is air maintained at an initial relative humidity (r.h.) of not less than about 50%.

10. The method of claim 7 wherein said heat is added by increasing the temperature between about 50° C. and 65° C. at a constant moisture level in said environment.

11. The method of claim 1 wherein said forming comprises controlled exposure to heat and solvent in a non-aqueous gaseous environment to adjust the glass transition point of said shearform sugar mass to ambient temperature.

12. The method of claim 1 wherein all bi-dimensionally stabilized crystalline frames have cross-sectional dimensions which are monodispersed.

13. The method of claim 12 wherein said monodispersed dimensions are microcrystalline.

14. The method of claim 13 wherein the size of said microcrystalline structure is not more than 50 μm.

15. The method of claim 14 wherein said size is not more than 10 μm.

16. The method of claim 1 wherein shearform amorphous sugar masses are provided by subjecting sugar feedstock material to high speed spinning on a spinning head in which said material is subjected to heat and shear sufficient to create flash flow and which discharges said amorphous sugar masses during spinning.

17. The method of claim 1 wherein masses of shearform amorphous sugar are provided by heating a non-solubilized sugar carrier sufficiently to provide internal flow conditions, and subjecting said carrier to disruptive fluid shear force to form said multiple shearform masses.

18. The method of claim 1 wherein said shearform amorphous sugar mass further comprises an additive whereby said additive is co-crystallized in said crystalline structure.

19. The method of claim 18 wherein said additive is a material which can be integrated into said amorphous sugar mass without reducing the amorphism of said sugar mass and without deteriorating said crystalline structure.

20. The method of claim 18 wherein said additive is selected from the group consisting of flavorants, bio-affecting agents, dyes, fragrances, food products, food ingredients, and other compatible agents.

21. The method of claim 1 which further comprises incorporating a crystallization modifier in said shearform amorphous sugar mass whereby said forming and said converting are enhanced.

22. The method of claim 21 wherein said crystallization modifier is selected from the group consisting of solvents, non-saccharide hydrophilic organic materials (NSHM's), and combinations thereof.

23. The method of claim 22 wherein said modifier is sugar solvent incorporated in said shearform amorphous mass in an amount of from about 0.25% to about 3.0% by weight.

24. The method of claim 22 wherein said modifier is a surface active agent or combination of surface active agents which have an HLB of at least 6.0.

25. The method of claim 1 which further comprises loading a non-solvent liquid in space created within said new crystalline sugar product by said converting.

26. The method of claim 25 wherein said non-solvent liquid is an oleaginous liquid.

27. The method of claim 26 wherein said oleaginous liquid is selected from the group consisting of vegetable oils, animal oils, flavor oils, medicament-containing oils, oleaginous, and mixtures thereof.

28. The method of claim 25 wherein said loading comprises transfer of liquid into said space by capillary action of said liquid in said space.

* * * * *

UNITED STATES PATENT AND TRADEMARK OFFICE
CERTIFICATE OF CORRECTION

PATENT NO. : 5,597,416
DATED : January 28, 1997
INVENTOR(S) : Fuisz, et al.

It is certified that error appears in the above-indentified patent and that said Letters Patent is hereby corrected as shown below:

<u>Column 10, Line 7,</u>   now reads "transaction", should read --transition--;

IN THE CLAIMS:

<u>Claim 1, Line 5,</u>   after "sugar mass", insert --in the presence of a controlled amount of water which initiates crystallization of amorphous sugar--;

<u>Claim 4, Lines 4-5,</u>   delete "in the presence of a controlled amount of water which initiates crystallization of amorphous sugar".

Signed and Sealed this

Seventeenth Day of June, 1997

*Attest:*

BRUCE LEHMAN

*Attesting Officer*   *Commissioner of Patents and Trademarks*